United States Patent [19]

Haugwitz et al.

[11] Patent Number: 4,803,202

[45] Date of Patent: Feb. 7, 1989

[54] SUBSTITUTED N-METHYL DERIVATIVES OF MITINDOMIDE

[75] Inventors: Rudiger D. Haugwitz, Bethesda; Venkatachala Naratanan, Gaithersburg, both of Md.; Leon H. Zalkow, Atlanta, Ga.; Howard M. Deutsch, Atlanta, Ga.; Leslie Gelbaum, Atlanta, Ga.

[73] Assignee: The United States of America as represented by the Secretary of the Department of Health and Human Services, Washington, D.C.

[21] Appl. No.: 25,062

[22] Filed: Mar. 12, 1987

Related U.S. Application Data

[62] Division of Ser. No. 604,136, Apr. 26, 1984, Pat. No. 4,670,461.

[51] Int. Cl.$^4$ .................... A61K 31/38; A61K 31/40; C07D 209/56
[52] U.S. Cl. ........................ 514/228.2; 514/232.5; 514/253; 544/57; 544/58.6; 544/142; 544/357
[58] Field of Search ............... 544/58.5, 121, 142, 544/359, 373, 372, 57, 58.6, 357; 514/232, 234, 253, 228.2, 232.5, 253

[56] References Cited

U.S. PATENT DOCUMENTS

| | | | |
|---|---|---|---|
| 3,366,642 | 1/1968 | Bradshaw | 548/119 |
| 4,271,074 | 6/1981 | Lohmann et al. | 548/419 X |
| 4,301,075 | 11/1981 | Lohmann et al. | 548/419 X |

OTHER PUBLICATIONS

Deutsch et al.: C.A., 102:37208z (1985).
Deutsch et al.; Acta Crystallogr.; Sect. C: Cryst. Struct. Commun. (1984), C40(11), pp. 1925–1927.
Roberts et al.; Basic Prin. of Org. Chem., 1965, pp. 49 and 70.
Walker; Formaldehyde, 3rd Ed., A.C.S. Monograph #120; pp. 374 & 391.
Retchert; Die Mannich Reaktion (1959); p. 104 [Springer-Verlag Berlin].
Greene; Protective Groups in Org. Syn. (1981); pp. 118, 121; 123; 126; 147.
Elderfield; Heterocyclic Compounds; p. 394, vol. 5, John Wiley, N.Y.
Morrison & Boyd; Org. Chem., 3rd Ed., p. 642, Allyn & Bacon, Boston.
Theilheimer; Aldehydes, 17, p. 117.
Houben-Weyl; Sauerstoff-Verbindungers II, Teil 1 (1954), pp. 414–415.
Pettit et al.; Can. J. Chem. 61, pp. 2291–2294 (1983).
Bryce-Smith et al.; J. Chem. Soc. (C): pp. 390–394 (1967).
Zhubanov et al., C.A., 91: 157542e; (1979).
Zhubanov et al., C.A., 95: 143256k; (1981).
Zhubanov et al., C.A., 88: 156390e (1978).
Imashev et al., C.A., 89; 46896n (1978).
Heinzl et al., C.A., 88: 90105g (1978).
Gilbert et al., C.A., 94: 17391w (1981).
Kardush et al., C.A., 79: 125535r (1973).
Arkhipova et al., C.A., 77: 100908k (1972).
Kanao, C.A., 83: 749q (1975).
Dore et al., C.A., 83: 188204k (1975).

*Primary Examiner*—Joseph P. Brust
*Attorney, Agent, or Firm*—Holman & Stern

[57] ABSTRACT

New substituted N-methyl derivatives of mitindomide and methods of preparing the same are disclosed. The novel compounds are water soluble and have anti-neoplastic activity.

5 Claims, No Drawings

SUBSTITUTED N-METHYL DERIVATIVES OF MITINDOMIDE

This is a divisional of application Ser. No. 06/604,136, filed Apr. 26, 1984, now U.S. Pat. No. 4,670,461.

BACKGROUND OF THE INVENTION

1. Technical Field

The present invention relates to certain derivatives of diimidestatin (mitindomide) which is a photosynthetic addition product of benzene and maleimide. More particularly, the present invention relates to N-methyl derivatives of diimidestatin and methods of preparing the same.

2. Description of the Prior Art

The photo-addition product of benzene and maleimide (hereinafter "mitindomide" NSC 284,356), has been reported to show strong inhibitory activity against certain experimental tumor systems [Pettit et al, Can. J. Chem. 61, 2291–2294, (1983)]. However, mitindomide is virtually insoluble in water. Therefore, such solvents as dimethyl sulfoxide (DMSO), N,N-dimethylformamide (DMF) or highly alkaline media and the like are employed to solubilize mitindomide. Of course, the use of organic solvents such as DMF and DMSO and aqueous media of high pH are hazardous to human health and toxic to mammalian tissues. Clearly these solubility characteristics of mitindomide severly restrict the utility of this compound where solubility in water or in neutral or mild aqueous media is desired. The applicants have now discovered that if certain derivatives of mitindomide are prepared in accordance with the present invention, the solubility of mitindomide, particularly in water, is substantially increased. Such increased water solubility of mitindomide derivatives allows their utilization, inter alia, in water soluble form which heretofore was not possible. An example of such utility is intraperitoneal or subcutaneous administration of mitindomide derivative as an antineoplastic agent in mammalian host. Other utility of these derivative compounds will be suggested to those skilled in the art.

Certain photoaddition products of benzene with N-phenylmaleimides substituted with electron-attracting groups have been reported by kardush et al (Chem. Abstr. 79, 125535r). Arkhipova et al (Chem. Abstr. 77, 100908K) have described the synthesis and the properties of a photoadduct of maleimide with benzene. Bryce-Smith et al, [J. Chem. Soc. (C) 390, (1967)], have described the stereochemistry of photoaddition of maleic anhydride to benzene. It is noted, however, that these references have little relevance to the present invention because they simply fail to teach or suggest the derivative compounds of mitindomide such as disclosed by the present invention.

SUMMARY OF THE INVENTION

It is, therefore, an object of the present invention to prepare derivative compounds of mitindomide.

It is a further object of the present invention to prepare substituted N-methyl derivatives of mitindomide.

It is yet another object of the present invention to prepare water-soluble derivatives of mitindomide.

A still further object of the present invention is to prepare antineoplastic compositions comprising mitindomide derivative as an active ingredient.

An additional object of the present invention is to provide a method of treating malignant tumors with substituted N-methyl derivatives of mitindomide.

Another object of the present invention is to describe methods of preparing substituted N-methyl derivatives of mitindomide.

These and other objects, features and many of the attendant advantages of the invention will be better understood upon a reading of the following detailed description and examples.

DETAILED DESCRIPTION OF THE INVENTION

The attainment of the above objects is made possible by the present invention which includes methods, compositions and compounds of formula (1) as shown below:

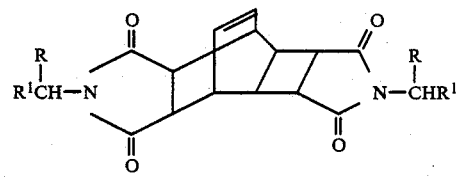

1 wherein R=hydrogen, lower alkyl, phenyl, benzyl or carboxylic acid group;

$R^1 = OR^2$ or $NR^3R^4$;

$R^2$ = hydrogen, $-COR^6$ $R^3, R^4$ = alkyl, hydroxy-substituted alkyl, halo-substituted alkyl, or $R^3$ and $R^4$ together with the nitrogen atom of $NR^3R^4$ form a ring such as

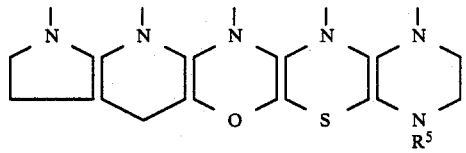

$R^5$ = alkyl or benzyl; and $R^6$ = alkyl, aminoalkyl, dialkylamino alkyl, amidoalkyl, dialkylamino alkyl, hydroxyalkyl, carboxyalkyl.

These novel derivatives are synthesized from the parent compound mitindomide. Either purified or unpurified photo adduct of benzene and maleimide (mitindomide) may be used. The preparation of the parent compound mitindomide, (benzene maleimide photosynthetic product) is known in the art and described in such publications as Pettit et al, Can. J. Chem. 61: 2291–2294, (1983) and references cited therein all of which are incorporated herein by reference. Compounds of structure 1 where $R^1$ is OH, i.e. 1a, may be prepared by reacting mitindomide with an aldehyde 2, preferably, aqueous formaldehyde. This hydroxymethylation reaction is conveniently performed using solvents, such as DMSO or DMF at temperatures ranging from about 0° C. to about 100° C. for periods of one hour to about one day.

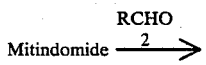

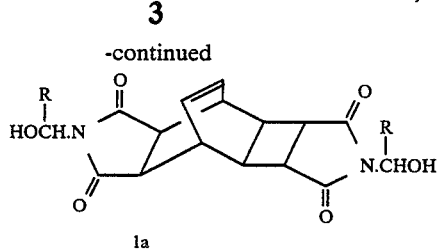

1a

Compounds of structure 1, where $R^1$ is $NR^3R^4$, i.e. 1b, can be prepared through aminomethylation i.e., the Mannich reaction. Several reviews detailing the scope and experimental conditions for the Mannich reaction are known among which the following are preferred:

a. Org. Reactions, 1, 303 (1942)
b. Chem. Reviews, 56, 286 (1956)
c. B. Reichert, Die Mannich Reaction, Springer Verlag, Berlin, 1959
d. Houben-Weyl's *Methoden Der Organischen Chemie*, Vol. 11/1 (1957)
e. Comprehensive Organic Chemistry, Vol. 1, 1040 (1979).

These references are incorporated herein and made a part hereof by reference. Thus, compounds of structure 1b can be synthesized either reacting the parent diimide together with the appropriate aldehyde RCHO, 2, and amine 3 (Route "A") or, preferably, reacting the hydroxymethyl compound 1a with the amine (Route "B") which are shown schematically hereunder:

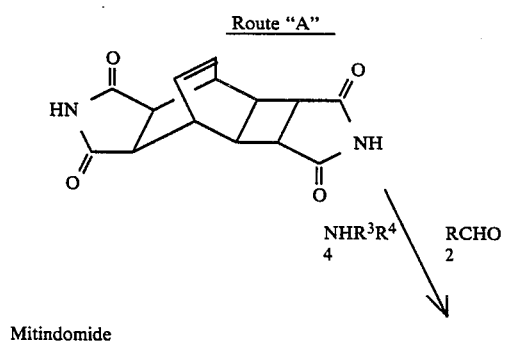

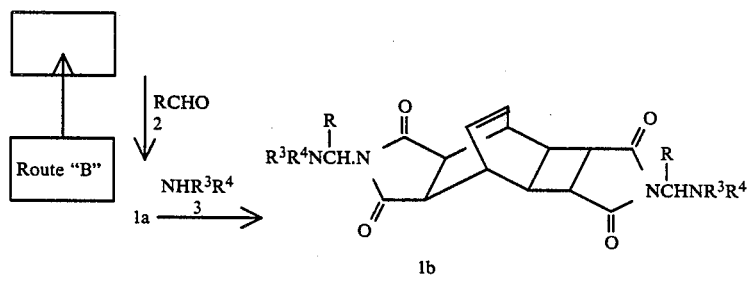

Compounds of structure 1b can form physiologically acceptable acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate inorganic acid. Illustrative are the hydrohalides, especially the hydrochloride and hydrobromide which are preferred, sulfate, nitrate, phosphate, oxalate, tartrate, acetate, maleate, rumarate, citrate, succinate, methanesulfonate, benzenesulfonate, toluenesulfonate, and the like.

Compounds of structure 1, where $R^1$ is $OR^6$, i.e., 1c, are conveniently prepared by coupling the hydroxymethyl compound 1a with an alkanoic acid 4 by one of the known procedures in which the acid is activated prior to reaction with the hydroxymethyl compound 1a, involving formation of a mixed anhydride, symmetrical anhydride, active ester, acid chloride or the like. The addition of pyridine or 4-N,N-dimethylaminopyridine frequently catalyzes the acylation step. Additional reaction conditions for this transformation can be found in published literature preferred among which are:

(a). Greene, Protective Groups In Organic Chemistry, 50 (1981)
(b). Drugs Of The Future, 6, 165 (1981)
(c). J. Med. Chem., 13, 607 (1970)
(d). Med. Res. Reviews, 1, 189 (1981).

These references are incorporated herein and made a part hereof by reference. A schematic reaction is shown herein below for the preparation of the compound of formula 1c.

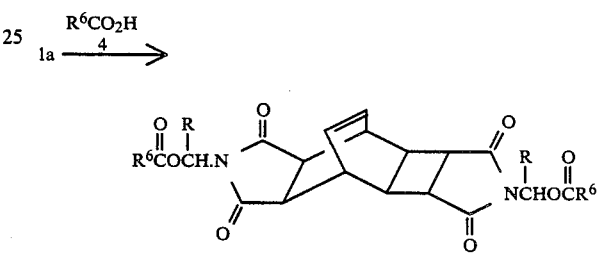

The following working examples will more fully illustrate the present invention. All temperatures are in Celcius scale unless specifically mentioned otherwise.

EXAMPLE 1

Preparation Of Parent Compound (Mitindomide, NSC 284356), 4,8-Ethenopyrrolo[3',4':3,4]cyclobut[1,2-f]-isoindole-1,3,5,7(2H,6H) tetrone, octahydro- A stirred solution of maleimide (200 g, 2.06 mol), acetophenone (250 mL, 258 g, 2.14 mol) and benzene (9.0 L) is irradiated at 60° with a 254 nm light source for 24 h. The precipitated solid is collected and then washed in succession with MeOH (500 mL) and $Et_2O$ (500 mL). The benzene filtrate is irradiated at 60° for a total of 6 additional days. During this period, additional product is collected at intervals of day 1, day 2, day 3, and day 6. The combined crops give a total of 225 g (80%) of the product. Additional reactions are carried out to give a total of 1245 g of crude material. A 174 g portion of this material is stirred in DMSO (600 mL) for 1 h, diluted with EtOH, collected, then washed in succession with DMSO-EtOH (100 mL: 200 mL) and EtOH (300 mL). At this point, the product still contains 1-2% DMSO after vacuum (100°) drying. The colorless solid is dissolved in 10% NaOH (600 mL), clarified by filtration, then acidified (15°) to pH 1 with 10% HCl. The precipitated solid is collected, washed in succession with water (600 mL), EtOH (600 mL), and $Et_2O$ (600 mL), then dried in vacuo at 80° to give 149 g (86% recovery) of product. The remainder of the material is processed in similar manner to give a total of 983 g of product which is contaminated with a hydrolyzed acid-/amide species. This material is washed by resuspension in saturated aqueous $NaHCO_3$. The solid is collected, washed in succession with $H_2O$ (4×500 mL) and EtOH (4×250 mL) then dried in vacuo at 40° to give 602 g (61% recovery) of purified product; mp>400°. Infrared: Nujol) Major bands: 3220, 2920, 2860, 1765, 1700, 1450, 1370, 1350, 1300, 1250, 1185, 1160, 780, 670 cm$^{-1}$. Ultraviolet: (p-Dioxane) max 253 nm (log 2.546); shoulder 260 nm (2.442); nmr: (TFA) 9.75 (s, 1H, —NH—); 9.55 (s, 1H, —NH—); 6.45 (m, 2H, vinyl H); 3.70-3.40 (m, 2H, methine H); 3.30-2.70 (m6H, methine H).

Anal. Calcd. for $C_{14}H_{12}N_2O_4$: C, 61.76; H, 4.44; N, 10.29; O, 23.51. Found: C, 61.58; H, 4.45; N, 10.10; O, 23.84.

EXAMPLE 2

4,8-Ethenopyrrolo[3',4':3,4]cyclobut[1,2-f]isoindole-1,3,5,7(2H,6H)-tetrone,-3a,3b,4,4a,7a,8,8a,8b-octahydro-2-,6-bis(hydroxymethyl)-

A mixture of 25.0 g (0.0919 mole) of the unpurified photo adduct of benzene and maleimide, 500 ml of DMF, and 20.7 ml (0.276 mole) of 37% aqueous formaldehyde is heated at 74° C. for two hours. After about 1.5 h, the initially turbid mixture becomes clear. The solvent is removed on a rotary evaporator using a vacuum pump, to leave a brown-yellow solid. The solid material is heated with about 1 L of water on a steam bath, with stirring to dissolve the solid. The cloudy solution is filtered hot and allowed to cool to room temperature and then to about 5° C. The white solid is isolated by filtration, dried in vacuo, to give 25.3 g (83%) of the title compound: mp 300° C.; vmax (Nujol) 3435, 3285, 1765, 1688, 1450 and 1055 cm$^{-1}$; nmr (DMSO-D$_6$) 6.37 (m, OH), 6.30 (m, olefinic H), 4.75 (d, J=5.9 Hz, $CH_2$), 4.64 (d, J=6.2 Hz, $CH_2$) and 3.21-2.60 (complex, ring H; nmr (TFA) 6.71 (m, olefinic H), 5.22 (s, $CH_2$), 5.41 (s, $CH_2$), 3.79-3.10 (complex, ring H); mass spectrum m/z 272 (M-2x$CH_2O$, 10%) and 78 (benzene, 100%).

Anal. Calcd. for $C_{16}H_{16}N_2O_6$x0.75$H_2O$: C, 55.57; H, 5.10; N, 8.10. Found C, 55.41: H, 5.16; N, 8.26.

EXAMPLE 3

4,8-Ethenopyrrolo[3'4':3,4]cyclobut[1,2-f]isoindole-1,3,5,7(2H,6H)-tetrone,3a,3b,4,4a,7a,8,8a,8b-octahydro-2,6-bis(N-methylpiperazinomethyl)-

Method A. A mixture of 6.70 g (0.0202 mol) of the above hydroxymethyl compound of Example 2, 4.47 ml (0.0404 mole) of N-methylpiperazine and 400 ml of DMF is heated at 73° C. for 18 h. The solvent is removed in vacuo and the off-white residue is recrystallized from warm water. The crude material is mixed with about 300 ml of water and heated to 55°-60° C. The cloudy solution is filtered warm and cooled to about 31 5° C. in an ice/isopropanol bath. The white solid is collected and dried in vacuo, to yield 4.50 g (45%) of the title compound; mp 250°-255° C. (dec), $v_{max}$ (KBr) 2940, 2800, 1765 and 1290 CM$^{-1}$; mass spectrum m/z 496 (M$^+$, 6%), 384 (M+112, 6%) and 70 (100%).

Anal. Calcd. for $C_{26}H_{36}N_6O_4$: C, 62.88; H, 7.31; N, 16.92. Found C, 62.55; H, 7.33; N, 16.63.

Method B. A mixture containing 2.00 g (0.00735 mole) of mitindomide, 1.14 ml (0.0154 mole) of 37% aqueous formaldehyde and 1.63 ml (0.0147 mole) of N-methylpiperazine is heated with 150 ml of DMF at 70° C. for about 6 h. The solvent is removed in vacuuo and the white solid is recrystallized as described in EXAMPLE 3 Method A, to yield 1.7 g (47%) of the title compound.

EXAMPLE 4

4,8-Ethenopyrrolo[3',4':3,4]cyclobut[1,2-f]isoindole-1,3,5,7(2H,6H)-tetrone,3a,3b,4,4a,7a,8,8a,8b-octahydro-2,6-bis(N-methylpiperazinomethyl)di-hydrochloride 2.50 g (0.00504 mole) of the title compound of EXAMPLE 3 is mixed with 200 ml of water and then there is added 100.8 ml (0.01008 mole) of 0.1N HCl. The resulting solution is freeze dried to yield 3.10 g of the title compound: mp 300° C.; $v_{max}$ (KBr) 3440(b), 1695, 1265 and 810 cm$^{-1}$.

Anal. Calcd. for $C_{26}H_{38}Cl_2N_6O_4$x1.5$H_2O$: C, 52.35; H, 6.93; Cl, 11.89; N, 14.09. Found C, 52.31; H, 6.93; Cl, 11.97; N, 14.06.

EXAMPLE 5

4,8-Ethenopyrro[3',4':3,4]cyclobut[1,2-f]isoindole-1,3,5,7(2H,6H)-tetrone,3a,3b,4,4a,7a,8,8a,8b-octahydro-2,6-bis(morpholinomethyl)

Following the procedure of EXAMPLE 3 but substituting morpholine for N-methylpiperazine, the title compound is obtained. Anal. Calcd. for $C_{24}H_{30}N_4O_6$x0.5$H_2O$: C, 60.11; H, 6.52; N, 11.68. Found C, 59.89; H, 6.41; N, 11.62.

EXAMPLE 6

4,8-Ethenopyrrolo[3',4':3,4]cyclobut[1,2-f]isoindole-1,3,5,7(2H,6H)-tetrone,3a,3b,4,4a,7a,8,8a,8-octahydro-2,6-bis(thiomorpholinomethyl)

Following the procedure of EXAMPLE 3 but substituting thiomorpholine for N-metylpiperazine, the title compound is obtained.

Anal. Calcd. for $C_{24}H_{30}N_4O_4S_2 \times 0.5H_2O$: C, 56.34; H, 6.11; N, 10.95; S, 12.53. Found C, 56.40; H, 6.07; N, 11.02; S, 12.68.

EXAMPLE 7

4,8-Ethenopyrrolo[3',4':3,4]cyclobut[1,2-f]isoindole-1,3,5,7(2$\underline{H}$,6$\underline{H}$)-tetrone,3a,3b,4,4a,7a,8,8a,8b-octahydro-2,6-bis(N,N-didethylaminomethyl)

Following the procedure of EXAMPLE 3 but substituting diethylamine for N-methylpiperazine, the title compound is obtained, mp 240° C.

Anal. Calcd. for $C_{24}H_{34}N_4O_4 \times 0.33H_2O$: C, 64.26; H, 7.79; N, 12.49. Found: C, 64.25; H, 7.64; N, 12.40.

EXAMPLE 8

4,8-Ethenopyrrolo3',4':3,4cyclobut[1,2-f]isoindole-1,3,5,7(2$\underline{H}$,6$\underline{H}$)-tetrone,3a,3b,4,4a,7a,8,8a,8b-octahydro-2,6-bis(acetyloxymethyl)

2 g of title compound from EXAMPLE 2 is acetylated with a mixture of pyridine-acetic anhydride to yield upon standard work-up 76% of product. Recrystallization from hot acetic acid furnishes the analytically pure title compound, mp 288°–290° C.

Anal. Calcd. for $C_{20}H_{20}N_2O_8$: C, 57.69; H, 4.84; N, 6.73. Found C, 57.35; H, 4.91; N, 6.58.

EXAMPLE 9

4,8-Ethenopyrrolo[3',4':3,4]cyclobut[1,2-f]isoindole-1,3,5,7(2$\underline{H}$,6$\underline{H}$)-tetrone,3a, 3b, 4,4a,7a,8,8a,8b-octahydro-2-,6bis(2-aminoacetyloxymethyl)

A mixture of 5.85 g of carbonyldiimidazole and 6.33 g of t-butyloxycarbonyl glycine is dissolved in 150 ml of dry DMF is allowed to stand for one hour. To this solution is added 2.8 g of the title compound from EXAMPLE 2. After one hour the solvent is removed in vacuuo, and the residue dried overnight in vacuuo. Then 150 ml of cold water is added and the mixture is stirred until the precipitated matter can be filtered. The solid is washed with water and dried to give 3.5 g of impure solid. A sample, 2.5 g, is chromatographed on 100 g of silica and the desired compound is eluted with 3% methanol in chloroform (one spot on TLC). The white solid (1.50 g) is mixed with 20 ml of 25% trifluoroacetic acid in chloroform and after standing 30 min at room temperature is evaporated to dryness. The syrup is dissolved in 20 ml of water and freeze dried to yield 1.3 g (32%) of the title compound as the trifluoroacetate salt mp dec, $v_{max}$(KBr) 3440, 3050, 2960, 1770, 1685 and 1200 cm$^{-1}$; $^1$H-nmr (D$_{20}$) 6.36 (m, vinyl H), 5.62 (s, NCH$_2$O) 5.51 (s, NCH$_2$O), 3.38 (s, NCH$_2$C), 3.38 (s, NCH$_2$C), 3.39, 3.01, 2.90 and 2.74 (bs, ring H).

Anal, Calcd. for $C_{24}H_{24}N_4O_{12}F_6$: C, 42.74; H, 3.59; N, 8.31. Found C, 42.50; H, 3.64; N, 8.24.

EXAMPLE 10

4,8-Ethenopyrrolo[3',4':3,4]cyclobut[1,2-f]isoindole-1,3,5,7(2$\underline{H}$,6$\underline{H}$)-tetrone,3a,3b,4,4a,7a,8,8a,8b-octahydro-2-,6-bis(succinyloxymethyl)

To a chilled (5° C.) solution of 4.0 g of the title compound from EXAMPLE 2 in 200 of dry pyridine is added 12.0 g of succinic anhydride. After one hour the solvent is removed in vacuuo, and 100 ml of water added. After good stirring, the mixture is cooled to about 5° C. and the product collected by filtration, washed with water and dried. This material, 4.3 g (67%) showed mp greater than 300° C. $v_{max}$(KBr) 3450, 3050, 2840, 1780 and 1710 cm$^{-1}$; nmr(DMSO-D$_6$) 12.2 (bs, CO$_2$H), 6.30 (m, olefinic H), 5.36 (s, CH$_2$O) 5.26 (s, CH$_2$O), 3.2–2.1 (complex, ring H and CH$_2$).

Anal. Calcd for $C_{24}H_{24}O_{12}N_2$: C, 54.14; H, 4.54; N, 5.26. Found: C, 54.20; H, 4.60; N, 5.26.

A 2.4 g sample of the title compound is mixed with 150 ml of water (not soluble) and the pH adjusted to 6.33 by addition of solid sodium bicarbonate. The clear solution is freeze dried to yield 2.8 g of white powder which is readily soluble in water.

EXAMPLE 11

4,8-Ethenopyrrolo[3',4':3,4]cyclobut[1,2-f]isoindole-1,3,5,7(2$\underline{H}$,6$\underline{H}$)-tetrone,3a,3b,4,4a,7a,8,8a,8b-octahydro-2-,6-bis(2-carboxyacetyloxymethyl)

A mixture of 6.0 g the title compound from EXAMPLE 1, 4.3 g of glyoxylic acid and 200 ml of DMF is heated at 70° C. for two hours. The solvent is removed in vacuuo, the residue dissolved in 100 ml of water and freeze dried to give 9.9 g of white solid. A 2.8 g sample of this material is dissolved in 150 ml of dry pyridine and 6.3 ml of acetic anhydride added. After three days at room temperature the solvent is removed in vacuuo, the residue dissolved in a small amount of water and passed over a column of Dowex 50W-X8 resin (H+form). The effluent was freeze dried to give 2.6 g (77%) of the title compound mp greater than 300° C.; $v_{max}$(KBr) 3450, 2950, 1780, 1720 and 1625 cm$^{-1}$; nmr (D$_2$O) 6.7 (s, HCO), 6.58 (s, HCO), 6.38 (m, vinyl H), 3.4–2.7 (complex, ring H), and 2.17 (bs, CH$_3$).

Anal. Calcd. for $C_{22}H_{20}N_2O_{12} \times 2.4H_2O$ C, 48.25; H, 4.56; N, 5.12. Found: C, 48.25; H, 4.50; N, 5.38.

A 2.5 g sample of the title compound is dissolved in 50 ml of water and the pH adjusted to 6.11 with solid sodium bicarbonate. The solution is freeze dried to yield 2.7 g of a pale yellow solid which is soluble in water.

EXAMPLES 12–21

Following the procedure of the indicated Example, and substituting the starting material having the substituents indicated below, the following compounds of Examples 12–21 as shown in Table 1 are obtained.

TABLE 1

[Structure 1: mitindomide derivative with R, R¹CHN, OR, NCHR¹ groups]

| Example # | Procedure for Example | R | R¹ | R² | (SALT) R³ | R⁴ | R⁵ | (SALT) R⁶ |
|---|---|---|---|---|---|---|---|---|
| 12 | 8 | H | OR² | COR⁶ | — | — | — | $(CH_2)_4 CH_3$ |
| 13 | 8 | H | OR² | COR⁶ | — | — | — | $C(CH_3)_3$ |
| 14 | 8 | $CH_2C_6H_5$ | OR² | COR⁶ | — | — | — | $O(CH_2)_2CN(C_2H_5)_2$ |
| 15 | 8 | H | OR² | COR⁶ | — | — | — | $CH_2N(CH_3)_2$ |
| 16 | 9 | H | OR² | COR⁶ | — | — | — | $CHNH_2CH_2C_6H_5$ (HCl) |
| 17 | 3 Method A | $CH_3$ | $NR^3R^4$ | — | $(CH_2)_4$ | | — | — |
| 18 | 3 Method B | H | $NR^3R^4$ | — | $(CH_2)_5$ | | — | — |
| 19 | 3 Method B | H | $NR^3R^4$ | — | $(CH_2)_2N(CH_2)_2$ | | $R^5$ $CH_2C_6H_5$ | — |
| 20 | 3 Method B | H | $NR^3R^4$ | — | $(CH_2)_2Cl$ | $(CH_2)_2Cl$ (HBr) | — | — |
| 21 | 3 Method B | H | $NR^3R^4$ | — | $(CH_2)_3OH$ | $(CH_2)_3OH$ | — | — |

Determination Of Anti-Tumor Or Anti-Neoplastic Activity

Anti-tumor or anti-neoplastic activity of the novel derivatives of the present invention is determined by using the murine test system for screening anti-cancer compounds as standardized by the National Cancer Institute, Bethesda, Md., U.S.A., and described in Cancer Chemotherapy Reports, 3 (2) 1-103 (1972) which publication is incorporated herein by reference.

The results of biological testing are shown in Tables 2, 3 and 4.

The data in Tables 2-4 clearly demonstrate the antineoplastic activity of the Mannich base congeners of the present invention. It is noted that although the intraperitoneal mode of administration of the novel derivatives is preferred, other modes of parenteral administration, e.g. subcutaneous, intravenous, etc., are, of course, possible and included within the purview of this invention. Similarly, although water has been used as a vehicle for the administration of the compounds of the present invention, other pharmaceutically acceptable vehicles, e.g. saline, buffers, and other aqueous media may also be used for the administration of these compounds together with adjuvants, agents or additives commonly employed in the preparation of pharmaceutical compositions. Examples of such agents, additives and adjuvants that may be employed are listed in Instruction 14, Screening Data Summary Interpretation and Outline of Clinical Screen. Drug Evaluation Branch, NCI. and are incorporated herein by reference.

Having described several embodiments of the novel derivatives of mitindomide according to the present invention, it is believed that other modifications, variations and changes will be suggested to those of ordinary skill in the art in light of the disclosure herein. It is, therefore, understood that all such variations, modifications and changes are included within the purview and scope of this invention as defined by the appended claims.

TABLE 2

BIOLOGICAL ACTIVITY AND WATER SOLUBILITY

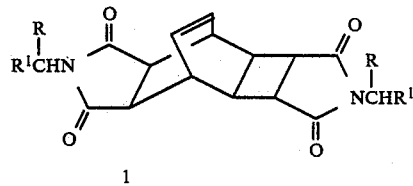

| Example | (NSC No.) | IP P388, Days 1-9 DOSE | & T/C | H₂O-Sol. % (g per 100 ml H₂O) |
|---|---|---|---|---|
| 2 | (361,429) | 50 | 208,195 | 0.8 |
| 8 | (363,226) | 400,200 | 208(1/5),180 | 0.1 |
| 11 | (367,922) | 200 | 175,125 | 5 |
| 10 | (370,153) | | * | 2 |
| 3 | (361,813) | 100 | 211,200 | 1.5 |
| 4 | (364,188) | 68.8 | 172 | 10 |
| 6 | (361,814) | 200 | 194.166 | 0.1 |
| 5 | (361,815) | 100,50 | 174,141 | 0.1 |
| 7 | (364,189) | 200 | 125,139 | 0.1 |
| 9 | (372,209) | | * | 2 |

*TEST RESULTS NOT AVAILABLE

TABLE 3

COMPARISON OF MITINDOMIDE AND MANNICH BASE CONGENERS AGAINST THE S.C. IMPLANTED L1210 LEUKEMIA IN MICE (CD2F1)

| Compound | Dose (mg/kg, ip days 1-9) | Expt. 1 Wt. Change (g.) | MST (days) | ILS (%) | Expt. 2 Wt. Change (g.) | MST (days) | ILS (%) |
|---|---|---|---|---|---|---|---|
| Controls | | 1.3 | 8.2 | | 0.4 | 10.7 | |

TABLE 3-continued
COMPARISON OF MITINDOMIDE AND MANNICH BASE CONGENERS AGAINST THE S.C. IMPLANTED L1210 LEUKEMIA IN MICE (CD2F1)

| Compound | Dose (mg/kg, ip days 1–9) | Expt. 1 Wt. Change (g.) | Expt. 1 MST (days) | Expt. 1 ILS (%) | Expt. 2 Wt. Change (g.) | Expt. 2 MST (days) | Expt. 2 ILS (%) |
|---|---|---|---|---|---|---|---|
| Mitindomide[a] | 138.9 | | | T | | | T |
| | 83.3 | −5.6 | 8.7 | 6 | −5.6 | | T |
| | 50.0 | −4.3 | 15.8 | 92 | −4.2 | 25.3 | 136[c] |
| | 30.0 | −3.8 | 12.3 | 50 | −1.6 | 15.3 | 42 |
| | 18.0 | 0.0 | 10.0 | 21 | −0.1 | 12.0 | 12 |
| Methylpiperazine | 166.7 | | | T | −4.9 | 25.0 | 133[c] |
| Congener | 100.0 | −5.3 | 20.0 | 143 | −3.1 | 18.5 | 72 |
| Example 3 | 60.0 | −4.2 | 14.0 | 70 | −0.7 | 12.3 | 14 |
| | 36.0 | −1.0 | 9.3 | 13 | −0.4 | 11.3 | 5 |
| | 21.6 | −0.3 | 8.7 | 6 | 0.2 | 11.8 | 10 |
| Dihydrochloride | 191.2 | | | T | −6.6 | | T |
| Salt | 114.7 | −4.7 | 19.3 | 135 | −4.0 | | T |
| Example 4 | 68.8 | −4.2 | 14.3 | 74 | −2.9 | 17.0 | 58 |
| | 41.3 | −1.6 | 12.3 | 50 | −1.5 | 13.0 | 21 |
| | 24.8 | −0.2 | 9.7 | 18 | 0.3 | 12.0 | 12 |

[a]Experimental formulation of mitindomide was used (NaOH + mannitol).
[b]Vehicle for Example 3 and Example 4 was water.
[c]2/6 Day 30 "cures".
MST = Median Survival time
ILS = Increased life span
S.C. = Subcutaneous
IP. = Intraperitoneal

TABLE 4
COMPARISON OF MITINDOMIDE AND MANNICH BASE CONGENERS AGAINST THE IP IMPLANTED L1210 LEUKEMIA IN MICE (CD2F1)

| Compound | Dose (mg/kg, IP days 1–9) | Expt. 1 Wt. Change (g.) | Expt. 1 MST (days) | Expt. 1 ILS (%) | Expt. 2 Wt. Change (g.) | Expt. 2 MST (days) | Expt. 2 ILS (%) | Expt. 3 Wt. Change (g.) | Expt. 3 MST (days) | Expt. 3 ILS (%) |
|---|---|---|---|---|---|---|---|---|---|---|
| Controls | | 2.2 | 8.7 | | 1.0 | 8.0 | | 0.4 | 8.2 | |
| Mitindomide | 138.9 | −5.6 | | T | | | T | −5.5 | | T |
| | 83.3 | −2.5 | 9.3 | 6 | −5.8 | 9.0 | 12 | −4.5 | 8.0 | −3 |
| | 50.0 | 0.2 | 14.0 | 60 | −3.9 | 16.3 | 103 | −2.8 | 21.0 | 156 |
| | 30.0 | 1.2 | 13.0 | 49 | −3.1 | 13.3 | 66 | −2.2 | 15.3 | 86 |
| | 18.0 | 2.3 | 9.0 | 3 | −0.7 | 8.8 | 10 | 0.3 | 9.3 | 13 |
| Methylpiperazine | 166.7 | −5.2 | 6.3 | T | | | T | −5.2 | 21.0 | 156 |
| (EXAMPLE 3) | 100 | −2.9 | 12.0 | 37 | −4.8 | 19.3 | 141 | −3.1 | 16.0 | 95 |
| | 60 | −0.4 | 12.0 | 37 | −4.4 | 14.0 | 75 | −1.3 | 12.0 | 46 |
| | 36 | 1.7 | 9.2 | 5 | −0.5 | 9.0 | 12 | 0.2 | 9.0 | 9 |
| | 21.6 | 1.9 | 9.1 | 4 | 0.7 | 8.3 | 3 | 0.2 | 9.0 | 9 |
| Dihydrochloride | 191.2 | | | T | | | T | −7.1 | | T |
| (EXAMPLE 4) | 114.7 | −2.6 | 9.0 | 3 | −5.3 | 16.8 | 110 | −4.6 | 20.0 | 143 |
| | 68.8 | −1.7 | 16.0 | 83 | −4.1 | 14.3 | 78 | −3.2 | 18.0 | 119 |
| | 41.3 | 1.4 | 10.8 | 24 | −2.6 | 11.8 | 47 | −1.5 | 11.0 | 34 |
| | 24.8 | 2.5 | 8.9 | 2 | 0.8 | 8.4 | 5 | 0.3 | 9.0 | 9 |

Experimental formulation of NSC 284356 was used (NaOH + mannitol).
Vehicle for Example 3 and Example 4 was water.
In expt. 1 Example 3 reported insoluble at 60 mg/kg and higher.
IP = Intraperitoneal

What is claimed is:

1. A compound of the formula:

wherein
R = hydrogen, lower alkyl, phenyl, benzyl, or carboxylic acid group;
wherein
each $R^1$ is the same and are selected from the group consisting of:

wherein
$R^5$ = alkyl or benzyl; and physiologically acceptable acid-addition salts thereof.

2. The compound of claim 1 wherein said compound is in the form of a physiologically acceptable acid-addition salt.

3. The compound of claim 1 wherein said acid-addition salt is selected from the group consisting of hydrohalide, sulfate, nitrate, phosphate, oxalate, tartrate, acetate, maleate, fumarate, citrate, succinate, methanesulfonate, benzenesulfonate and toluenesulfonate.

4. An antineoplastic composition for treating implanted L1210 leukemia, comprising an antineoplastically effective amount of the compound of claim 1 as an active ingredient and a pharmaceutically acceptable additive or carrier.

5. A method of treating mammals implanted with L1210 leukemia comprising administering to said mammals an antineoplastically effective amount of the compound of claim 1.

* * * * *